United States Patent [19]
Wildman

[11] Patent Number: 6,142,776
[45] Date of Patent: Nov. 7, 2000

[54] LINGUAL ORTHODONTIC BRACKET AND METHOD OF USE

[76] Inventor: Alexander J. Wildman, 6 Devon Mill Pl., The Woodlands, Tex. 77382

[21] Appl. No.: 09/439,749

[22] Filed: Nov. 15, 1999

[51] Int. Cl.[7] ...................................................... A61C 3/00

[52] U.S. Cl. .................................................. 433/10; 433/8

[58] Field of Search ................................ 433/8, 9, 10, 11, 433/12, 13, 14, 15, 16, 17

[56] References Cited

U.S. PATENT DOCUMENTS

| 4,337,037 | 6/1982 | Kurz . |
| 4,531,911 | 7/1985 | Creekmore . |
| 4,669,981 | 6/1987 | Kurz . |

*Primary Examiner*—Nicholas D. Lucchesi
*Attorney, Agent, or Firm*—Marger Johnson & McCollom, P.C.

[57] ABSTRACT

A lingual orthodontic bracket includes a bonding pad for attaching said bracket to a lingual side of a tooth. A base member is connected to the bonding pad, and opposing first and second wings are connected to the base member for engaging opposite end portions of an O-ring. An archwire slot is defined in the base member between the first and second wings and has an entrance in a direction of the second wing, opposing first and second walls, and a base wall positioned opposite the entrance in a direction of the base member. The archwire slot is configured to receive an archwire in a direction substantially directed from the second wing to the base member at an acute angle to a plane of the bonding pad. A pair of O-ring slots are defined in opposite lateral sides of the base member at a location where the base member connects to the second wing in such a manner that the connection between the base member and the second wing forming a T-shaped member in plan view. Each O-ring slot has a first wall substantially aligned with the entrance to the archwire slot and a second wall spaced apart from the first wall in the direction of the second wing by a distance approximately equal to the cross-sectional width of the Oring to retain the archwire in the archwire slot by a compression-resistant force. A method for removably securing an archwire within the archwire slot of the lingual orthodontic bracket is also provided.

17 Claims, 2 Drawing Sheets

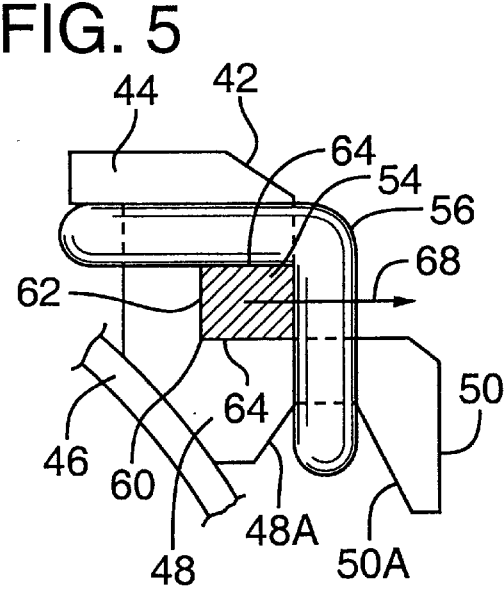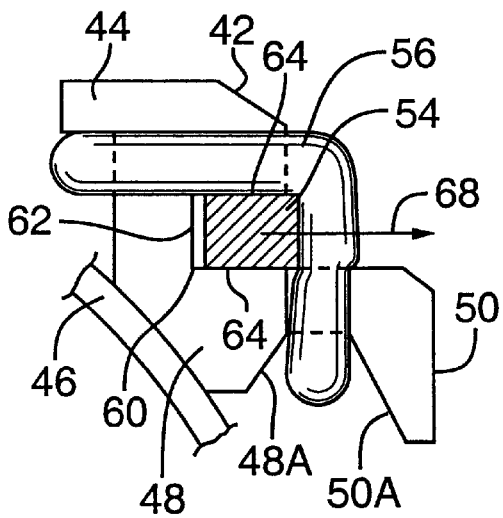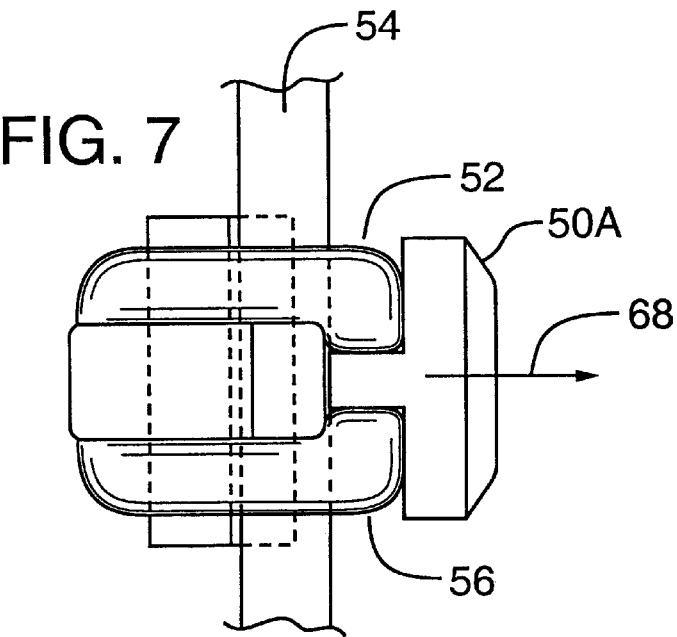

LINGUAL ORTHODONTIC BRACKET AND METHOD OF USE

BACKGROUND OF THE INVENTION

This invention relates generally to orthodontic devices. More specifically, this invention relates to lingual orthodontic brackets.

Two primary types of orthodontic brackets have been used in the prior art, namely, labial and lingual brackets. As the name implies, labial brackets are positioned on the labial surfaces of a person's teeth. The most conventional type of labial bracket is a symmetric dual-wing bracket as shown in FIGS. 1 and 2. Referring to FIGS. 1 and 2, this bracket 1 has a bonding pad 4, a base member 6, and two opposing wings 12. An archwire slot 10 is located between the two wings 12 and receives an archwire 8 at a right angle to the plane of the bonding pad 4. After the archwire 8 is in place within the archwire slot 10, an O-ring 14 is placed around one of the wings 12 and then stretched over the opposing wing 12 to retain the archwire 8 in place. This single tie configuration allows the elastic tensile forces of both halves of the O-ring 14 to symmetrically oppose a force (represented by arrow 16) tending to remove the archwire 8 from the archwire slot 10. O-rings 14 must typically be replaced at least every six weeks because their elastomeric material becomes degraded over time as a result of the chemical environment of the mouth. When it is time to replace the O-rings 14, the O-rings 14 can be removed and replaced one at a time by simply disengaging the end portions of the O-ring 14 from the wings 12. The conventional labial bracket 1 is therefore simple to use.

Lingual brackets are attached to the lingual surfaces of a person's teeth. Lingual brackets are desirable because they are not readily noticeable to an outside viewer. Unlike the labial brackets described above, however, the conventional lingual brackets, as shown in FIGS. 3, 3A, 4, and 4A, are generally difficult or inefficient to use. Referring to FIGS. 3, 3A, 4, and 4A, a conventional lingual bracket 20 is asymmetric and comprises a bonding pad 24, a base member 36, and opposing occlusal (or incisal) and gingival wings 32 and 38, respectively. The conventional lingual bracket also includes an archwire slot 30 located between the two wings 32 and 38 and angled toward the gingival wing 38. The archwire slot 30 has an entrance in the direction of the gingival wing, opposing first and second walls, and a base located opposite the entrance in the direction of the base member 36. Examples are shown in U.S. Pat. Nos. 4,337,037 and 4,669,981 to Kurz. The gingival wing 38 can include an elongated extension with a knob end as shown in Kurz '981 or can be T-shaped to serve as a hook for inter-maxillary elastics.

FIGS. 3 and 4 show the most typical tying arrangement of the conventional lingual bracket, i.e., double-tied. Referring to FIGS. 3 and 4, an O-ring 34 is generally double-tied around the archwire 26 of the conventional lingual bracket 20. In a double-tie configuration, the O-ring 34 must first be placed around the base 36. Only after the O-ring 34 is positioned around the base 36 is the archwire 26 inserted into the archwire. slot 30 in a direction at an acute angle to the plane of the bonding pad 24. A second end portion of the O-ring 34, located between the gingival wing 38 and the bonding pad 24, is then stretched over the gingival wing 38, around the archwire 26 and back over the occlusal wing 32, forming a substantially U-shaped O-ring configuration, as viewed from a side view. The tensile forces of both halves of the O-ring 34 retain the archwire 26 within the archwire slot 30 by nearly symmetrically opposing a force (represented by arrow 22) tending to disengage the archwire 26 therefrom.

Unfortunately, there are disadvantages with the double tied lingual bracket of the prior art. First of all, as with labial brackets, the O-rings of lingual brackets must be replaced frequently. Unlike the single tied labial brackets, however, the process for replacing the O-ring on a double tied lingual bracket is complex. To replace the O-ring, the second end portion of the O-ring must first be stretched back over the occlusal and gingival wings such that the O-ring surrounds only the base member. Then, the archwire must be removed from the archwire slot. Only then can the old O-ring be completely removed from the bracket. Finally, a new O-ring must be attached using the steps described above for attaching the original O-ring. This process must be repeated for each of the lingual brackets needing O-ring replacement.

Another serious disadvantage with the use of double tied conventional lingual brackets is that the O-ring must be stretched much further than that of the labial bracket. Excessive stretching further reduces the life of the O-ring. Furthermore, to accommodate this amount of stretching, the double tied lingual bracket O-ring must be highly elastic. This increased elasticity adversely affects its tensile strength, and hence its ability to oppose forces that remove the archwire from its slot.

To avoid some of these disadvantages associated with double tying the O-ring of the conventional lingual brackets, a single tie configuration for the same brackets has been attempted. Although it is possible to single tie the archwire into the archwire slot of the conventional lingual bracket, using a single tie configuration with the conventional lingual bracket is disadvantageous because it results in a very weak retaining force. FIGS. 3A and 4A show a conventional lingual bracket using a single tie configuration. As shown in FIGS. 3A and 4A, in a conventional lingual bracket 20 with a single tie configuration, the O-ring 34 is placed over the gingival wing 38 and then stretched over the occlusal wing 32. In this configuration, a force (represented by arrow 22) acting to disengage the archwire 26 from the archwire slot 30 is only weakly opposed by the O-ring 34 for several reasons. First of all, only the portion of the O-ring 34 extending from the occlusal wing 32 has a tensile force which directly opposes the archwire's 26 movement away from the slot 30. The other portion of the O-ring 34, which is attached around the gingival wing 38 at approximately a right angle to the first portion, is free to slide along the gingival wing 38. It does not, therefore, provide any significant retaining force. Further disadvantageous is the fact that the O-rings used to single tie the archwire into the archwire slot of the conventional lingual bracket must be replaced more frequently than those used in a double tie configuration because they only have one portion of the O-ring that directly opposes the force tending to remove the archwire from the archwire slot. These drawbacks associated with conventional lingual brackets have made their use much less desirable than the labial brackets, despite the fact that many people prefer them aesthetically.

It should be noted that all of the dual wing prior art brackets described above rely solely on tensile properties of the O-ring to retain the archwire within the archwire slot. Neither prior art bracket contemplates the use of other properties of the O-ring which might aid in retaining the archwire within its slot.

The industry has been unable to provide to the orthodontic profession a lingual bracket which allows easy O-ring attachment and replacement while providing sufficient retaining strength. Furthermore, the industry has relied solely on the tensile elastic properties of O-rings to retain the archwire within the archwire slot of both lingual and labial brackets. What the industry needs, therefore, is a lingual bracket which facilitates easy attachment and replacement of O-rings without compromising retaining strength. The profession would also be benefited by a method of retaining an archwire within the archwire slot of a lingual bracket which uses a more stretchresistant O-ring.

SUMMARY OF THE INVENTION

According to the needs of the industry, one object of the present invention is to facilitate easy attachment and replacement of O-rings on a lingual orthodontic bracket without sacrificing retention efficiency.

Another object of the present invention is to utilize a more stretch-resistant O-ring to retain an archwire within an archwire slot of a lingual orthodontic bracket.

This invention provides an improved lingual orthodontic bracket which takes advantage of compression-resistant properties of an O-ring, in addition to its tensile elasticity, to secure an archwire within an archwire slot in a single tie configuration. It does this by providing a choke point which is formed by positioning the T-shaped member of the gingival wing close enough to the archwire slot to allow a cross-section of the O-ring to be compressed by the dislodging force. Specifically, the lingual orthodontic bracket of this invention has a bonding pad for attaching said bracket to a lingual side of a tooth. A base member is connected to the bonding pad. Opposing first, i.e., occlusal or incisal, and second, i.e., gingival, wings are connected to the base member to receive opposite end portions of an O-ring. An archwire slot is defined in the base member between the first wing and the second wing and is angled toward the second wing. An O-ring slot is defined transverse to the archwire slot in a lateral side of the base member between the base member and the second wing and is configured to receivingly engage a portion of the O-ring. The O-ring slot is arranged to form a choke point so that a force tending to remove the archwire from the archwire slot will compress the O-ring cross-sectionally between the archwire and the second wing.

In operation, the archwire is positioned within the archwire slot, but a force tends to cause it to disengage from the archwire slot through an entrance thereof.

The O-ring is therefore attached between the first wing and the second wing such that the archwire is retained within the archwire slot by the O-ring. According to the preferred embodiment, the O-ring is stretched in a substantially L-shape configuration around the archwire from the first wing to the second wing, with a portion of the O-ring located in the O-ring slot. Thus configured, the O-ring opposes the force tending to remove the archwire from the archwire slot by both a tensile force and a compression resistant force.

A method for removably securing an archwire within an archwire slot of a lingual orthodontic bracket having a base member, opposing first and second wings, and an archwire slot positioned between the wings and canted toward the second wing is also provided. The method includes forming an O-ring slot on a lateral side of the base member between the base member and the second wing. An O-ring is removably attached around the first and second wings and over the archwire located within the archwire slot so that a force tending to remove the archwire from the archwire slot will be opposed by an elastic tensile force of the O-ring. The O-ring is further removably positioned within the O-ring slot such that the force tending to remove the archwire from the archwire slot is opposed by a cross-sectional compression resistant force of the O-ring.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 5 is a side view of an lingual orthodontic bracket according to a preferred embodiment of the present invention.

FIG. 6 is another side view of the lingual orthodontic bracket shown in FIG. 5 further illustrating a force tending to remove the archwire from the archwire slot and also illustrating an O-ring's resistance of that force using both tensile elastic and crosssectional compression resistant properties thereof.

FIG. 7 is a plan view of the lingual orthodontic bracket shown in FIG. 5.

DETAILED DESCRIPTION

Figure 1:
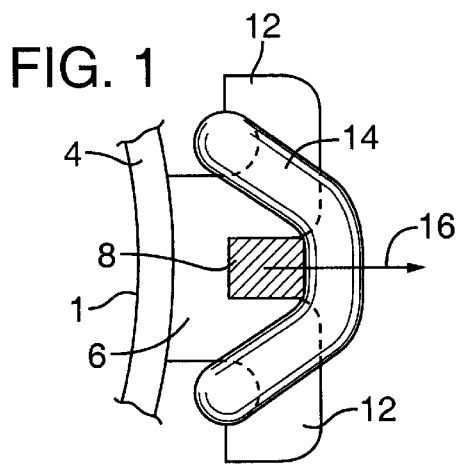
FIG. 1 is a side view of a conventional symmetrical dual-wing labial orthodontic bracket.
Figure 2:
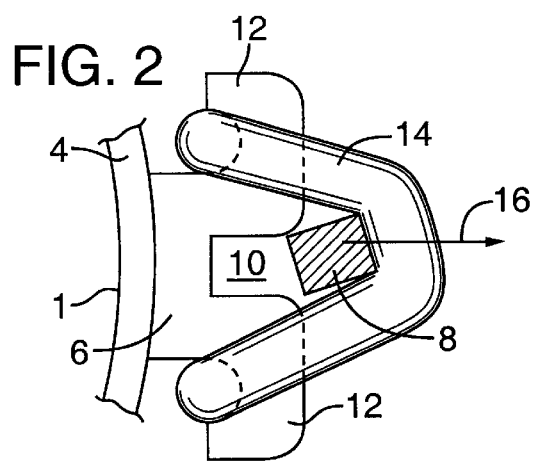
FIG. 2 is another side view of the conventional symmetrical dual-wing labial orthodontic bracket shown in FIG. 1 illustrating a force tending to remove an archwire from an archwire slot and also illustrating the O-ring's resistance of that force.
Figure 3:
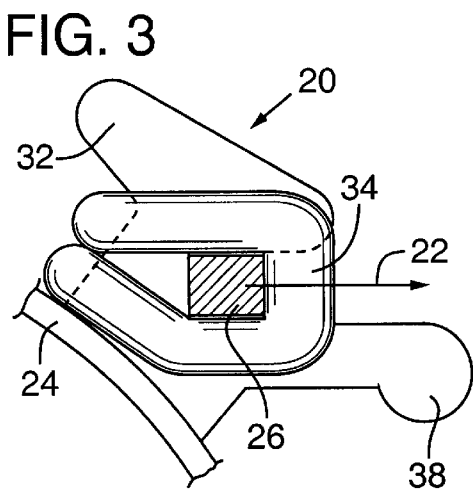
FIG. 3 is a side view of a conventional asymmetrical dual-wing lingual orthodontic bracket having a double tie configuration.
Figure 4:
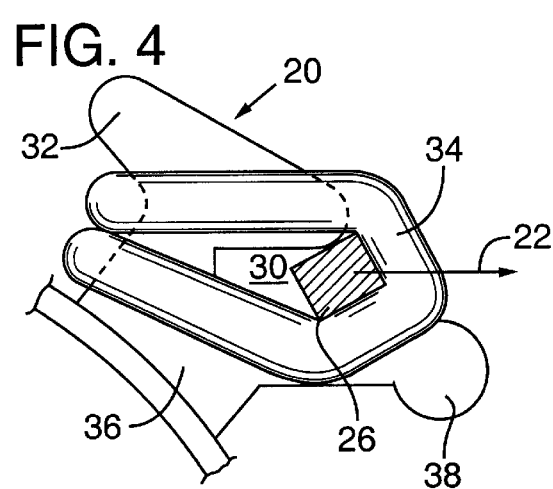
FIG. 4 is another side view of the conventional asymmetrical dual-wing lingual orthodontic bracket having the double tie configuration shown in FIG. 3, further illustrating a force tending to remove the archwire from the archwire slot and also illustrating the O-ring's resistance of that force.
Figure 3A:
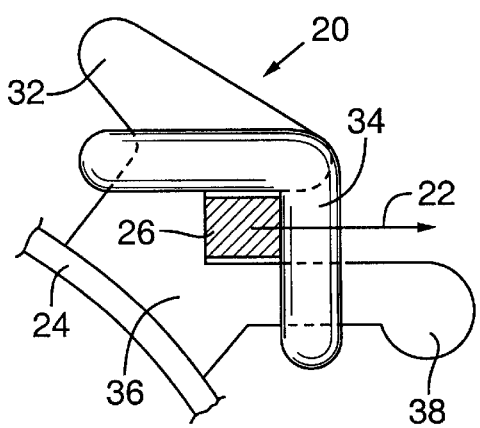
FIG. 3A is a side view of a conventional asymmetrical dual-wing lingual orthodontic bracket having a single tie configuration.
Figure 4A:
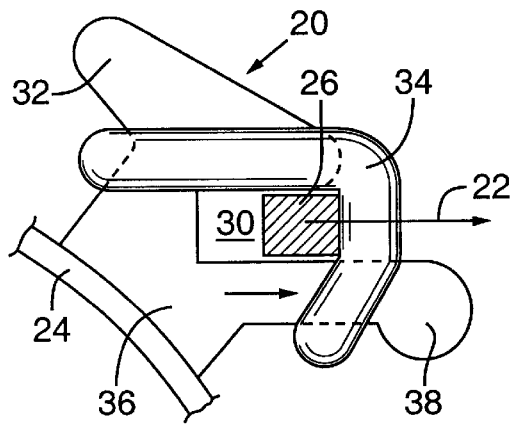
FIG. 4A is another side view of the conventional asymmetrical dual-wing lingual orthodontic bracket having the single tie configuration shown in FIG. 3A, further illustrating a force tending to remove the archwire from the archwire slot and also illustrating the O-ring's resistance of that force.

A preferred embodiment of the present invention will now be described with reference to FIGS. 5, 6, and 7. FIGS. 5 and 6 are side views, and FIG. 7 is a plan view, of the lingual orthodontic bracket according to a preferred embodiment of the present invention. Referring to FIGS. 5 and 7, a lingual orthodontic bracket 42 includes a bonding pad 46 with a base member 48 attached thereto. Opposing first and second wings 44 and 50 are connected to the base member. The first (i.e., occlusal or incisal) wing 44 and second (i.e., gingival) wing 50 are configured to receivingly engage opposite end portions of an O-ring 56 in a single tie configuration.

An archwire slot 60 is defined in the base member 48 between the two wings 44 and 50 in a direction angled toward the second wing 50. The archwire slot 60 has an entrance in the direction of the second wing, opposing first and second walls 64, and a base wall 62 located opposite the entrance in the direction of the base member. The base wall 62 is formed from a surface of the base member 46. The archwire slot 60 is configured to receive an archwire 54 through its entrance in a direction oriented at an acute angle to a plane of the bonding pad 46.

The lingual orthodontic bracket of this invention is also provided with a pair of O-ring slots 52 defined along opposite lateral sides of the base member 48 between the base member 48 and the second wing 50, where the base member 48 connects to the second wing 50. The O-ring slots 52 of the preferred embodiment are defined transverse to the archwire slot 60 and provide a choke point for the O-ring 56 as a result of their positioning in relation to the archwire slot 60. Specifically, the O-ring slots 52 cause the connection between the base member 48 and the second wing 50 to appear as a T-shaped member when viewed in plan view, as shown in FIG. 7. The T-shaped member is positioned close enough to the archwire slot 60 so that a cross-section of the O-ring 56 will be compressed between the archwire 60 and the second wing 50 as a result of a force tending to remove the archwire 54 from its slot 60.

Specifically, in the preferred embodiment, a portion of the O-ring 56 fits within each of the O-ring slots 52. A first wall of the O-ring slot 52 is substantially aligned with the entrance of the archwire slot 60. A second wall of the O-ring slot 52 is spaced apart from the first wall in the direction of the second wing 50 by a predetermined distance approximately equal to the cross-sectional width or diameter of the O-ring 56. Both the second wing 50 and the base member 48 can be provided with sloping surfaces 50A and 48A, respectively, to urge the O-ring 56 into the O-ring slots 52. Having the O-ring slot 52 positioned adjoining the entrance to the archwire slot 60 enables the compression resistant properties of the O-ring to resist a force tending to remove the archwire 54 from the archwire slot 60. This arrangement of features also allows the O-rings used in conjunction with this invention to be significantly more resistant to stretching than those used in the double tie configuration of the prior art because they do not need to be stretched nearly as far.

In operation, the archwire 54 is inserted into and positioned within the archwire slot 60 through the entrance thereof. The archwire 54 has just slightly smaller dimensions than the archwire slot 60. The O-ring 56 is then placed over either the first wing 44 or the second wing 50 and stretched around the archwire 54 and over its opposing wing. The O-ring 56 is thereby removably engaged by the wings 44 and 50 in a substantially L-shaped single tie configuration when viewed from a side view. Portions of the O-ring are also thereby positioned within the O-ring slots 52.

FIG. 6 further illustrates the operation and advantages of the invention. Referring to FIG. 6, a force (represented by arrow 68) tends to remove the archwire 54 from the archwire slot 60. The O-ring 56 opposes that force 68 in two ways. First, as the archwire 54 attempts to disengage from the archwire slot 60, the O-ring 56 is stretched. Because of its elastic material, the O-ring 56 desires to return to its original length and a tensile elastic force opposing the force 68. The invention therefore utilizes the tensile elastic force of the O-ring to oppose the force 68 tending to remove the archwire 54 from its slot 60. Secondly, as the archwire 54 attempts to disengage from its slot 60, it pinches the portions of the O-ring 56 located at the choke points created by second walls of the O-ring slots 52. The O-ring 56 resists this compressive force and desires to return to its original shape. The cross-sectional compression resistant force created by the compression of the O-ring 56 against the opposing walls of the O-ring slots 52 thereby also opposes the force 68 tending to remove the archwire 54 from the archwire slot 60. Because the O-ring slots 52 are located on a different level than the archwire 54, the compression force asserted by the archwire on the O-ring is a shear-type compressive force.

The lingual orthodontic bracket 42 of this invention may be formed in any way conventionally known in the art, such as by metal casting, but is preferably formed using a metal injection molding (MLM) technique. Having described and illustrated the principles of the invention in a preferred embodiment thereof, it should be apparent that the invention can be modified in arrangement and detail without departing from such principles. I claim all modifications and variations coming within the spirit and scope of the following claims.

What is claimed is:

1. A lingual orthodontic bracket comprising:
    a bonding pad for attaching said bracket to a lingual side of a tooth;
    a base member connected to the bonding pad;
    opposing first and second wings connected to the base member for engaging opposite end portions of an O-ring;
    an archwire slot defined in the base member between the first wing and the second wing for receiving an archwire, the archwire slot being angled in a direction toward the second wing; and
    an O-ring slot for receivingly engaging a portion of the O-ring, said O-ring slot defined along a lateral side of the base member between the base member and the second wing and arranged so that a force tending to remove the archwire from the archwire slot compresses the O-ring cross-sectionally between the archwire and the second wing.

2. The lingual orthodontic bracket according to claim 1, further comprising:
    an archwire located within the archwire slot;
    an O-ring stretched between the first and second wings and extending across an entrance to the archwire slot to retain the archwire within the archwire slot; and
    the O-ring slot having a wall spaced from the entrance to the archwire slot by a predetermined distance in the direction of the second wing.

3. The lingual orthodontic bracket according to claim 2, wherein the O-ring is attached in a substantially L-shaped configuration around the archwire.

4. The lingual orthodontic bracket according to claim 2, wherein the O-ring is positioned and stretched across the archwire slot entrance so as to oppose the force tending to remove the archwire from the archwire slot by both a tensile elastic force and a cross-sectional compressive resistant force.

5. The lingual orthodontic bracket according to claim 2, wherein the predetermined distance is approximately equal to the cross-sectional diameter of the O-ring.

6. The lingual orthodontic bracket according to claim 1, wherein a connection between the base member and the second wing appears substantially T-shaped from a plan-view.

7. The lingual orthodontic bracket according to claim 1, wherein the second wing comprises a sloping surface for urging the O-ring into the O-ring slot.

8. The lingual orthodontic bracket according to claim 1, wherein the O-ring slot comprises a first wall substantially aligned with the entrance to the archwire slot and a second wall positioned apart from and opposing the first wall by a distance approximately equal to a diameter of the O-ring in the direction of the second wing.

9. The lingual orthodontic bracket according to claim 1, wherein the archwire slot is configured to receive an archwire in a direction oriented at an acute angle in relation to a plane of the bonding pad.

10. The lingual orthodontic bracket according to claim 1, wherein the O-ring slot comprises a pair of slots positioned on opposite lateral sides of the base member.

11. The lingual orthodontic bracket according to claim 10, wherein each of the O-ring slots comprises a first wall located along a plane substantially flush with the entrance of the archwire slot.

12. The lingual orthodontic bracket according to claim 11, wherein each slot further comprises a second wall positioned opposite the first wall by a distance approximately equal to a cross-sectional diameter of the O-ring.

13. A method for removably securing an archwire within an archwire slot of a lingual orthodontic bracket having a base member, and opposing first and second wings, the archwire slot being positioned between the wings and canted toward the second wing, said method comprising:

forming an O-ring slot on a lateral side of the base member between the base member and the second wing;

removably attaching an O-ring around the first and second wings and over the archwire positioned within the archwire slot so that a force tending to remove the archwire from the archwire slot will be opposed by an elastic tensile force of the O-ring; and removably positioning the O-ring within the O-ring slot, so that the force tending to remove the archwire from the archwire slot will be opposed by a cross-sectional compression resistant force of the O-ring.

14. The method according to claim 13, wherein the O-ring is stretched around the archwire in a substantially L-shaped configuration.

15. The method according to claim 14, further comprising positioning the O-ring slot so that a leg portion of the O-ring lies flush with an entrance of the archwire slot.

16. The method according to claim 13, wherein the O-ring slot comprises a first wall substantially aligned with an entrance of the archwire slot and wherein the O-ring slot has a width approximately equal to the cross-sectional diameter of the O-ring.

17. A lingual orthodontic bracket comprising:

a bonding pad for attaching said bracket to a lingual side of a tooth;

a base member connected to the bonding pad;

opposing first and second wings connected to the base member for engaging opposite end portions of an O-ring;

an archwire slot defined in the base member between the first and second wings and configured to receive an archwire in a direction substantially directed from the second wing to the base member at an acute angle to a plane of the bonding pad, said archwire slot having an entrance in a direction of the second wing, opposing first and second walls, and a base wall positioned opposite the entrance in a direction of the base member;

a pair of O-ring slots defined in opposite lateral sides of the base member at a location where the base member connects to the second wing, the connection between the base member and the second wing forming a T-shaped member in plan view; and each O-ring slot having a first wall substantially aligned with the entrance to the archwire slot and a second wall spaced apart from the first wall in the direction of the second wing by a distance approximately equal to the cross-sectional width of the O-ring to retain the archwire in the archwire slot by a compression-resistant force.

* * * * *